United States Patent [19]
Morrow

[11] Patent Number: 5,334,383
[45] Date of Patent: Aug. 2, 1994

[54] ELECTRICALLY HYDROLYZED SALINES AS IN VIVO MICROBICIDES FOR TREATMENT OF CARDIOMYOPATHY AND MULTIPLE SCLEROSIS

[75] Inventor: Robert E. Morrow, Salt Lake City, Utah

[73] Assignee: Medical Discoveries, Inc., Logan, Utah

[21] Appl. No.: 527,321

[22] Filed: May 23, 1990

[51] Int. Cl.$^5$ .............................................. A61K 37/50
[52] U.S. Cl. .................................... 424/94.4; 435/817
[58] Field of Search ........................ 435/817; 424/94.4

[56] References Cited

U.S. PATENT DOCUMENTS

| | | | |
|---|---|---|---|
| 3,616,355 | 10/1971 | Themy et al. | 204/149 |
| 4,236,992 | 12/1980 | Themy et al. | 204/278 |
| 4,316,787 | 2/1982 | Themy | 204/242 |
| 4,968,616 | 11/1990 | Inoue et al. | 424/94.4 |
| 4,970,216 | 11/1990 | Deckner et al. | 424/94.4 |
| 4,976,959 | 12/1990 | Berger, Jr. et al. | 424/94.4 |
| 5,028,588 | 7/1991 | Hoffman et al. | 514/6 |

FOREIGN PATENT DOCUMENTS

| | | | |
|---|---|---|---|
| 55-87712 | 7/1980 | Japan | 424/94.4 |
| 56-32422 | 4/1981 | Japan | 424/94.4 |
| 1259001 | 10/1989 | Japan | 424/94.4 |

*Primary Examiner*—Douglas W. Robinson
*Assistant Examiner*—Deborah K. Ware
*Attorney, Agent, or Firm*—Thorpe, North & Western

[57] ABSTRACT

A method of treating antigen related infections is disclosed which comprises subjecting a dilute normal saline solution to electrical hydrolysis with adequate voltage to produce a solution containing bioactive microbicidal atoms, radicals or ions selected from the group consisting of chloride, ozone, hydroxide, hypochlorite, peroxide, chlorine dioxide, and oxygen with corresponding amounts of molecular hydrogen and sodium and hydrogen ions. The solution is balanced to normal saline with hypertonic saline. The injecting of effective amounts of the balanced solution intravenously into a warm blooded animal affected by an antigenic related infection results in a microbicidal action which mimics or enhances action of the free radicals produced in vivo as a result of respiratory bursts. The balanced saline solution may be injected along with the administration of moderating and/or neutralizing amounts of antioxidants or reducing agents such as catalase, superoxide dismutase, MPO or other suitable peroxidase, glutathione, glutathione peroxidase, ascorbic acid or other suitable agents. The moderating antioxidants and/or neutralizing agents are preferably administered orally prior to the administration of the saline solution with additional amounts of ascorbic acid being administered intravenously following injection of the saline. The microbicidal effects of the saline solution may be enhanced by the coadministration of effective amounts of colchicine or other enhancing agents.

5 Claims, No Drawings

ELECTRICALLY HYDROLYZED SALINES AS IN VIVO MICROBICIDES FOR TREATMENT OF CARDIOMYOPATHY AND MULTIPLE SCLEROSIS

BACKGROUND OF THE INVENTION

This application relates to the in vivo antimicrobial use of electrically hydrolyzed salines. More particularly, this invention relates to the treatment of antigen related infections in warm blooded animals by the intravenous injection of electrically hydrolyzed saline solutions which mimic or enhance the naturally occurring chemicals produced in vivo by the body in responding to such infections.

Phagocytic cells (neutrophils, monocytes, eosinophils, macrophages, and large granular lymphocytes, collectively called "killer cells") give off superoxide in what is called the "respiratory burst" which has an antimicrobial action and, if not properly controlled, can also cause tissue damage. The superoxide radical itself may not be directly responsible for the microbicidal action. Rather, this activity and any resultant tissue damage may be attributed to superoxide derivatives such as hydrogen peroxide, hydroxyl radical and possibly, singlet oxygen. Polymorphonuclear neutrophils and macrophages not only give off superoxide, leading to the production of hydrogen peroxide and hydroxyl free radical, but also generate hypohalous acids and N-chloroamines as one of their mechanisms which also destroy bacteria. These leukocytes consume oxygen which is transformed by membranous reduced nicotinamide adenine dinucleotide phosphate (NADPH) oxidase to superoxide.

The "respiratory burst" is observed as a dramatic increase in the consumption of oxygen and the activation of a membrane-associated NADPH oxidase. This oxidase reduces molecular oxygen to superoxide anions, which in turn dismutates to hydrogen peroxide. Superoxide and hydrogen peroxide can interact to give rise to the hydroxyl radical and possibly also to singlet oxygen. The superoxide anion, hydrogen peroxide, hydroxide radicals and singlet oxygen, all possess antimicrobial activity and are quite unstable. The respiratory burst continues during phagocytosis by polymorphonuclear leukocytes until engulfment is complete. The respiratory burst may also occur in leukocytes under various chemical influences in addition to phagocytosis.

The respiratory burst, although intimately connected with phagocytosis, is not an essential accompaniment to phagocytosis. Recent evidence suggests that free tissue macrophages and newly recruited monocytes, as distinguished from fixed tissue macrophages, can respond to lymphokines and phagocytic stimuli by mounting a respiratory burst. The failure of fixed tissue macrophages, such as Kupffer cells, to produce active metabolites of oxygen may be important in protecting tissues from damage during the scavenger functions of the macrophage. Many soluble agents, including antigen/antibody complexes, C5a, ionophores and tumor promoters, can trigger the respiratory burst without phagocytosis. The respiratory burst can also be triggered by opsonized particles or surfaces when phagocytosis is frustrated by the use of a drug such as cytochaiasin B. In addition to the reactive species of oxygen referred to above, i.e. superoxide anions, hydrogen peroxide, hydroxyl radicals, and singlet oxygen, there are a number of other potential microbicidal mechanisms in macrophages many of which are oxygen dependent. A major oxygen dependent system is mediated by myeloperoxidase (MPO), which catalyzes oxidation of a number of substances to hydrogen peroxide. MPO is the oxidase of neutrophils and the green color of pus is due to its presence. A cofactor in the MPO system is the iodide ion from the thyroid hormones, thyroxine or triiodothyronine. However, this microbicidal system sometimes also utilizes other halide ions such as bromide or chloride as cofactors in the place of iodide.

It is well documented that two free radicals of superoxide combine with hydrogen to form normal oxygen and hydrogen peroxide. This is known as the dismutation reaction with superoxide dismutase (SOD) acting as the catalyst. Unless hydrogen peroxide is denatured promptly with catalases or peroxidases, there is an interaction between superoxide and hydrogen peroxide leading to the production of the highly reactive hydroxyl radicals via pathways known as the Haber-Weiss or Fenton's reactions. Singlet oxygen is also generated by the removal of the unpaired electrons of the superoxide radical.

Leukocytes, in vivo, use the formation of superoxide, hydrogen peroxide, hydroxide radicals, singlet oxygen and halogenated products such as hypochlorous acid to destroy bacteria, fungi and viruses and perhaps also tumor cells. Other oxygen-dependent antimicrobial systems, unrelated to MPO, are also believed to rely on the production of hydrogen peroxide, superoxide anion, the hydroxyl radical and/or singlet oxygen to do the microbial killing in vivo. Some of these systems are not well documented but it is known that when such systems shut down or operate inefficiently, severe infections results.

There are also problems involved with over production or an excess of these radicals within the cells of the host. Hence, the body has provided means for mediating or neutralizing these products once they have performed their antimicrobial functions.

As previously mentioned SOD is effective in scavenging superoxide radicals (each containing an unpaired electron) in a simultaneous oxidation-reduction reaction with hydrogen called dismutation. Two superoxide radicals combine with two hydrogen atoms to form hydrogen peroxide and oxygen. Hydrogen peroxide is reduced by the enzymes catalase, glutathione peroxidase and MPO into oxygen and water.

Hence, in a normal functioning host, such as in a human or other warm blooded animal, there is an intra vivo interaction and balance maintained between respiratory bursts brought on by the presence of an invading foreign substance such as bacteria, virus or fungi accompanied by the formation of superoxide, hydrogen peroxide, hydroxyl radicals, singlet oxygen, hypohalous acids, and hypochlorite ions [collectively referred to as free radicals] with their accompanying antimicrobial actions and the mediating or neutralizing action of the enzymes SOD, MPO, glutathione, glutathione peroxidase, catalase, ascorbic acid and its salts and perhaps others.

There are situations when there is not sufficient free radicals present to accomplish their desired tasks. There are numerous bacterial, viral, fungal related syndromes and immunological disorders wherein it would be beneficial to have free radicals available to the cells for the short period required for their antimicrobial action followed by mediation and/or neutralization of the free radicals. Examples of such syndromes and/or immunological disorders are multiple sclerosis, cardiomyopathy (viral myocarditis), viral associated autoimmune diseases and perhaps even AIDS related syndromes. These are all diseases which are affected by slow, latent or temperate virus which have long incubation periods and, in some cases, have a low ratio of reported cases to infections. They are also diseases for which there is no known cure and usually slowly progress until they, or a concurrent opportunistic infection, results in the death of the host.

An infected host or patient may be treated by a variety of regimens which may alleviate the symptoms for a time. However, the immune system eventually is weakened to the point that it can no longer adequately contend with the invading or autoimmune related infections and the natural biocidal action in the cells ceases to function properly.

OBJECTS AND SUMMARY OF THE INVENTION

It is an object of the present invention to provide a method of treating antigenic related infections wherein the a solution is injected into the body of a warm blooded animal which mimics or enhances the naturally occurring free radicals produced by respiratory bursts in the cells in responding to such infections.

It is also an object of this invention to provide a method of treating antigenic related infections by injecting an electrolyzed saline solution containing free radicals into the bloodstream of a warm blooded animal along with the administration of moderating or neutralizing agents which enables the body to utilize such chemicals as microbiocides in the same manner as it does during in vivo respiratory bursts.

A still further object of this invention is to provide a method of treating antigenic related infections by the coadministration of electrolyzed saline solutions containing free radicals and colchicine into the bloodstream of a warm blooded animal along with the administration of moderating agents to enhance the ability of the body to utilize the free radicals as microbiocides.

These and other objects may be accomplished by means of first preparing a dilute normal saline solution, subjecting this solution to electrical hydrolysis with adequate voltage to produce an electrolyzed solution containing hydrogen, chlorine or chloride ions, ozone, sodium and hydroxide ions. The interaction of the electrolysis products results in a solution containing bioactive atoms, radicals or ions selected from the group consisting of chloride, ozone, hydroxide, hypochlorite, peroxide, chlorine dioxide, oxygen and perhaps others along with corresponding amounts of molecular hydrogen and sodium and hydrogen ions. The injecting of effective amounts of the electrolyzed solution intravenously into a warm blooded animal affected by an antigenic related infection results in a microbicidal action which mimics or enhances action of the free radicals produced in vivo as a result of respiratory bursts. The electrolyzed saline solution may be injected along with the administration of moderating and/or neutralizing amounts of antioxidants or reducing agents such as catalase, superoxide dismutase, MPO or other suitable peroxidase, glutathione, glutathione peroxidase, ascorbic acid or other suitable agent. The moderating anti oxidants and/or neutralizing agents may be administered just prior to, concurrent with or shortly following the administration of the electrolyzed saline solution.

Also, the antioxidants or neutralizing agents may be administered either orally, intravenously or parenterally. As used herein, the term parenterally refers to intramuscular administration. Additionally, the microbicidal effects of the electrolyzed solution may be enhanced by the coadministration of effective amounts of colchicine and perhaps other enhancing agents.

DETAILED DESCRIPTION OF THE INVENTION

The content of electrolyzed saline solutions has long been known as has the fact that such solutions are in vitro microbicides. Themy, U.S. Pat. Nos. 4,236,992 and 4,316,787 are drawn to a novel electrode, method and apparatus for electrolyzing dilute saline solutions to produce effective amounts of disinfecting agents such as chlorine, ozone and hydroxide ions. An apparatus for producing electrolyzed saline solutions is currently available under the tradename Ster-O-Lizer as manufactured and distributed by Ster-O-Lizer Manufacturing Corporation, 2109 West 2300 South in West Valley City, Utah. Laboratory reports and other data available from testing of electrolyzed saline solutions from various Ster-O-Lizer models have shown that it is effective in keeping water free of pathogenic organisms. Tests conducted in vitro further show that certain microorganisms, inclusive of Psudomonas agruginosa, Escherichia coli, Staphylococcus aureus, Candidia albicans, Salmonella typhi, and even HIV-1, are non-infectious after exposure to electrolyzed saline solutions.

Although it is known that electrolyzed saline solutions possess in vitro microbicidal activity it has long been thought that components in the electrolyzed solution, such as ozone and chlorine, are toxic to warm blooded animals and should not be utilized for in vivo purposes. It has now been found, however, that normal saline solutions, which have been subjected to electrolysis, can be injected into the vascular system provided modulating chemicals are also administered just as the phagocytic reactions in the immunosystem require catalysts to create a reaction to assist in the removal of a toxin. Therefore, in order to mimic or enhance the physiological action in immunological "respiratory bursts" to the generated microbicide, one or more of several modulating chemicals are added to the complete treatment. These modulating chemicals are administered before, concurrent with or after the electrolyzed saline and may be administered intraveneously, parenterally or, in some cases, orally. As used herein, the terms modulating and moderating are used interchangeably.

When the electrolyzed saline is injected into the vascular system of a warm-blooded animal it is transported rapidly throughout the system and passes intercellularly into cells affected by invading microorganisms. The components of the solution pass readily through cell walls and function in the manner described above for free radicals. Chlorine is thought to be present primarily as a chloride ion or as a hypochlorite ion. However, the primary microbicidal action of chlorine and its compounds comes through the formation of hypochlorous acid. This acid is formed upon the combining of free chlorine and water. Hypochlorites undergo hydrolysis with the formation of hypochlorous acid. The hypochlorous acid then decomposes to form hydrochloric acid and nascent oxygen. Nascent oxygen is a strong oxidizing agent having microbicidal action. Chlorine also interacts directly with intracellular substances as a microbicide. The hypochlorite ion is also microbicidal. Sodium hypochlorite has long been used as an antiseptic, disinfectant and sterilant. It has found use in dilute form, about 0.5% concentration, in surgery and in dissolving and deodorizing necrotic tissue. It has also been used to irrigate ragged or dirty wounds and as an antiseptic in certain peritoneal dialysis systems. Chlorine dioxide, in water, yields chlorine and hypochlorous acid. Chlorine dioxide, at a concentration of 0.0001% and maintained at a pH of about 7, will kill *E. coli* in about 6 seconds and the poliovirus in about one minute. It possesses about 2.5 times the oxidizing capacity of chlorine gas.

The intracellular actions of the hydroxide ion have previously been described.

The modulating chemicals are enzymes or reducing agents which interact with and reduce the active microbicidal agents to innocuous compounds. The enzymes are inclusive of, but not limited to, the superoxide dismutases (SOD), catalase and glutathione peroxidase. As previously stated, they function to remove the superoxides, peroxides and hydroxides that are formed in the cells. Otherwise oxygen toxicity results. These oxygen radicals are converted to hydrogen peroxide by Cu/Zn activated superoxide dismutases (SOD) in the cells. In a properly functioning system the hydrogen peroxide is then converted to oxygen and water by a catalase. If the hydrogen peroxide and the superoxide radical are allowed to combine, the more deadly hydroxide radical is formed.

The primary activated SOD in warm-blooded animals is Cu, Zn-superoxide dismutase. This metalloenzyme undergoes a reduction-oxidation cycle with the superoxide radical with the net result of dismutation of the superoxide radical to hydrogen peroxide and oxygen. The metals required for this activity are copper and zinc. Other forms, i.e. Mn-SOD and Fe-SOD, are also known but occur primarily in bacteria and cellular mitochondria. Without the presence of copper, the SOD enzyme is virtually inactive in the animal. The activity of the Cu, Zn-SOD enzyme can be suppressed by the too rapid accumulation of hydrogen peroxide. Therefore, it is essential that other enzymes which deplete hydrogen peroxide be functional within the cell to maintain SOD activity.

Catalase is a large molecular weight enzyme that contains four heme groups per molecule. Catalase is the primary enzyme necessary for the breakdown of hydrogen peroxide in the cell to oxygen and water and is found in all cells of the body that utilize oxygen.

Glutathione peroxidase (GSH-Px) has a selenium dependent form which contains four moles of selenium per mole of the enzyme. The oxidative role of this enzyme is similar to catalase in that it converts hydrogen peroxide to water and oxygen. Whenever catalase or glutathione peroxidase activity is impaired there can be a toxic build-up of peroxides. This, in turn, can lead to a build-up of the hydroxide radical. The non-selenium glutathione peroxidase (GSH-P) plays a role in controlling lipid peroxidation. The primary form of glutathione peroxidase within the red blood cell is the selenium dependent form.

Glutathione and ascorbic acid are both reducing agents involved in biological systems of oxidation.

Glutathione is a tripeptide of cysteine, glutamic acid and glycine. It is most often isolated from animal tissues in the form of it cuprous salt. The oxidized form is readily reduced by tissues to the sulfhydryl form. The latter from, in the presence of traces of copper gives up its hydrogen to molecular oxygen, becoming oxidized in turn. In other words, in the oxidized form it acts in the cells as a hydrogen acceptor and in the reduced form, as a hydrogen donor. The oxidized form is reduced by glutathione reductase. Glutathione appears to be an ubiquitous reducing agent involved in many intracellular redox reactions.

Ascorbic acid (Vitamin C) functions in a number of biochemical reactions, mostly involving oxidation. It is a reducing agent associated with the regeneration and maintenance of the connective tissue. Vitamin C has been shown to be an effective stimulator to the immune system. As a strong reducing agent it is used as an antioxidant to neutralize the oxidizing chemicals in the electrolyzed saline solution. Ascorbic acid is also a coenzyme for the oxidation of glutathione. Ascorbic acid is readily absorbed from the intestine. It is present in the plasma and is ubiquitously distributed in the cells of the body. Hence, it may be orally administered. However, intramuscular or intravenous injections of either ascorbic acid or sodium ascorbate may also be utilized when faster action is preferred.

Timely administration of one or more of these modulating agents prevents the toxic effects of excess amounts of oxidizing agents present in the electrolyzed saline solution.

The sterile saline solution that is treated in the electrolysis unit has an initial concentration of about 0.25 to 0.5% NaCl which is about one-fourth to one-half strength of normal or isotonic saline solution. Solutions of about 0.33% concentration are preferred. The saline solution is diluted with sterile distilled water to the desired concentration and subjected to electrolysis at sufficient voltage and time to produce an electrolyzed solution containing about 100 to 300 and preferably about 200 ppm $Cl^-$. Prior to intravenous injection, this solution is then adjusted back or balanced to normal saline solution concentration with sufficient hypertonic saline, e.g. 5% hypertonic saline solution. An effective amount of this balanced saline is injected intravenously and may vary greatly according to the antigen related disease being treated, the size of the warm-blooded animal, etc. For human beings the dosage of this balanced solution to be injected intravenously may vary from between about 10 to 80 cc's with a dosages of about 20–30 cc being preferred.

The amount of moderating agent to be administered will depend somewhat upon the method and time of administration. Dosages of moderating agents administered orally will be somewhat higher than if injected intravenously. Also, if the modulating agent is administered before injection of the electrolyzed saline, there must be sufficient time allowed for the modulating agent to be absorbed and carried into the bloodstream to the site where it can reduce the free radicals from the electrolyzed saline after they have accomplished their microbicidal mission.

The dosage of modulating agent or agents to administer is not necessarily stoichiometric with the free radicals of the electrolyzed saline and may initially have to be determined empirically. There should be sufficient modulating agent in the system to prevent the free radical components of the electrolyzed saline from causing irreparable tissue damage. For that reason, it may be beneficial to administer modulating agents such as the superoxide dismutase, catalase, L-glutathione, glutathione peroxidase, MPO and ascorbic acid orally for a period of time prior to the injection of the electrolyzed saline to provide the availability of adequate amounts of these agents in the cells at the time the electrolyzed saline is injected. However, it is equally important that the free radical components be available to perform their desired microbicidal function before being suppressed or deactivated by the modulating agents. Therefore, oral dosages of superoxide dismutase varying from about 5,000 to 60,000 units per day may be administered. Catalase, MPO and glutathione peroxidase dosages my vary between about 10,000 to 120,000 units per day. Glutathione may be administered in amount ranging from 10 to 120 mg per day. Ascorbic acid or its salts may be administered over a wide range of from about 50 to 5000 mg per day. Preferably, additional acid is administered intravenously shortly after the injection of the electrolyzed saline to make sure that the unreacted oxidative components of the saline are reduced and/or neutralized. Based on the above guideline one skilled in the art can readily determine what an effective amount of modulating agent is.

By injecting the electrolyzed saline and administering the modulating agent in the manner described above, there is created in the cells the same elements as are created naturally in the body to fight infections. In other words, the electrolyzed saline solution mimics the action of the free radicals produced during the respiratory burst from the macrophages and monocytes. Similarly, the modulating agents mimic the action of the enzymes produced by macrophages and monocytes as reducing agents to neutralize the oxidants. This results in a straight forward attack on the microorganisms within the host cell by the injected chemicals.

The addition of the alkaloid colchicine to the electrolyzed saline may also prove beneficial as an adjunct in preventing replication of the invading microorganisms.

Colchicine, [N-(5,6,7,9-Tetrahydro-1,2,3,10-tetramethoxy-9-oxobenzo[a]heptalen-7-yl)acetamide] $C_{22}H_{25}NO_6$ is a major alkaloid of Colchicum autumnale. It is an anti-inflammatory agent used primarily as a gout suppressant and in the treatment of Familial Mediterranean Fever. It functions by inhibiting the migration of granulocytes into an inflamed area reducing the release of lactic acid and proinflammatory enzymes that occur during phagocytosis thereby breaking the cycle that lead to the inflammatory response. The neutrophils and leukocytes produce glycoproteins which bind cells and may be a cause of acute inflammation. Colchicine prevents either the production by or release from leukocytes of glycoproteins. It also produces a temporary leukopenia that is soon replaced by a leukocytosis, sometimes due to a striking increase in the number of basophilic granulocytes and may have the same action in increasing lymphocyte production. The site of action is apparently directly on the bone marrow. Colchicine is an antipyretic, lowering body temperature. It also increases the sensitivity of the body to CNS depressants, depresses the respiratory center, enhances the response to sympathomimetic agents, constricts blood vessels and induces hypertension by central vasomotor stimulation. It is well tolerated in moderate dosage and, although not a corticosteroid, acts much like cortisone in suppressing the immunosystem without the attendant high risk and side effects of corticosteroids. In low dosages, colchicine actually works as an immune system stimulant helping to relieve an overworked immunosystem.

While not known for a certainty it is believed the colchicine functions in the present invention primarily in preventing the release of glycoproteins which bind cells and breaks the cycle of inflammatory response. Other secondary effects may be that it functions as an antimitotic, antiviral agent, as a mild immunosuppressant and produces a leukocytosis by stimulating the bone marrow.

To understand why the use of colchicine to prevent the release of glycoproteins in important to the present invention, the following information regarding HIV and AIDS is beneficial. This extreme viral infection is popularly referred to as AIDS (acquired immune deficiency syndrome). However, it is more appropriately an HIV (human immunodeficiency virus) infection leading to AIDS. This disease proceeds through various stages from HIV exposure to HIV infection and on to development of AIDS. These stages are classified by Redfield, et al. in an article entitled "The Walter Reed Staging Classification for HTLV-III/LAV Infection" published in the New England Journal of Medicine, Volume 314, Page 131, January, 1986 and are referred to as the Walter Reed (WR) classification. They are thus referred to as WR0 through WR6. The WR0 classification means there has been exposure to the HIV virus although there are no symptomatic indications. WR1 means there is a positive HIV antibody and/or virus determination but no other symptoms. A WR2 classification is characterized by chronic lymphadenopathy or swollen lymph nodes in addition to positive HIV antibody and/or virus determination. A WR3 classification is reached when the T4-cell count drops below 400 cells per cubic millimeter of blood and stays down. The normal T4-cell count is about 800. There may or may not be chronic lymphadenopathy in WR3 through WR6 classifications but the T4-cell count stays below 400. A patient moves to the WR4 stage after partial sub-clinical (asymptomatic) defects are found in delayed hypersensitivity, i.e. the ability to react to skin tests that are a barometer of immune functioning. The line into WR5 is crossed when the patient completely fails to respond to the skin test or when thrush (a fungal disease of the mouth) develops. Lymphadenopathy and abnormalities of the T4-cell and skin tests must persist for at least three months to serve as valid criteria. Patients enter into the WR6 stage and are said to have AIDS when opportunistic infections, which occur because the immune system has broken down develop elsewhere in the body. Typical opportunistic infections include Kaposi's sarcoma, cryptococcal meningitis, cytomegatovirus (causing blindness) and classic Pneumocystis carinii pneumonia.

The HIV virus is a retrovirus which does not per se cause death of its host. However, the presence of the HIV virus contributes to the decline of T4-cells in the body. The T4 lymphocytes, or T4-cells, recognize foreign antigens or infected cells. Upon recognition, the T4-cells help activate another set of white blood cells called B-lymphocytes. These B-cells then multiply and produce specific antibodies that bind to the infected cells and other organisms containing the antigen. The binding of the antibodies to the antigen containing cells or organisms inactivates and/or destroys those cells or organisms.

The T4-cells have other functions as well. They orchestrate cell-mediated immunity by killing infected cells with cytotoxic cells such as T8 lymphocytes and white cells known as killer cells . The T4-cells also influence mobile scavenger cells known as monocytes and macrocytes. These scavengers engulf infected cells and foreign particles and secrete a variety of cytokines. The cytokines are small but highly potent proteins that modulate the activity of many cell types, including T and B cells. The T4-cells also secrete cytokines on their own which stimulates the proliferation of T and B cells in the body.

From the above, it is apparent that the loss of T4-cells can seriously impair the body's ability to fight antigen caused diseases and viral infections in particular. The eradication of these invading organisms requires a highly-orchestrated cell-mediated response. Without T4-cells this immune response does not function satisfactorily.

According to Redfield et al., "HIV Infection: The Clinical Picture", Scientific American, 259:90, October, 1988, there is a balance of power between the HIV virus and the immune system arranged by the T4-cells. From the WR0 (exposure stage) to the WR1 stage the HIV virus increases rapidly at which point the immune system begins to respond. By the time the WR2 stage is reached the viable virus in the body has dropped dramatically with the concomitant rise in scavengers, macrophages, T-cells, B-cells, antibodies and other immune system members. The immune system remains somewhat in control throughout the WR2 and into the WR3 stages although there is a gradual rise in HIV. However, by the time the WR4 stage is reached the HIV has begun to overwhelm the immune system and the T4-cells become so depleted that the balance of power switches and from that point on the HIV replicates wildly, overwhelming the remaining T4-cells and any vestiges of immune defense.

How the HIV virus infects and kills T4 cells raises many questions leading to certain theories and/or conclusions. Infection begins as a protein, gp120, on the vital envelope binds tightly to a protein known as the CD4 receptor on the cell surface. The virus then merges with the T4 cell and transcribes its RNA genome into double-strand DNA. The viral DNA becomes incorporated into the genetic material in the nucleus of the cell and directs the production of new viral RNA and viral proteins which combine to form new virus particles. These particles bud from the cell membrane and infect other cells.

Under certain circumstances the HIV virus can multiply prodigiously in the helper T cells and kill them, suggesting that viral replication is the main cause of cell destruction. In particular, it has been found that HIV replication and cell deaths increase when infected helper T cells become activated, as they do when they take part in an immune response to other infections. Thus, the very immunological process that should defeat the HIV virus has the opposite effect of increasing the proliferation of the virus.

Further investigation reveals an apparent paradox, i.e. HIV replication could be demonstrated in only a small fraction of T4 cell collected from HIV infected patients. The cells killed by replication alone might hamper the immune system somewhat but that would not cause the severe immune deficiency seen in AIDS. However, another mechanism for T4 cell destruction, and which is compatible with the present invention, may be explained by the formation of syncytia or massive bodies consisting of many merged cells having multinuclei. Syncytia develops after a single cell becomes infected with HIV and produces viral proteins, including gp120, which is displayed on the surface of the infected cell. Because gp120 and the CD4 receptor of the T4 cells have a high affinity for each other, uninfected T4 cells can agglomerate and/or bind to the infected cell and merge with it. The resulting syncytium cannot function and dies. The original infected cell is killed, but so are myriad uninfected T4 cells that could otherwise be used to attack and kill the HIV virus.

Furthermore, in a process that is unique to the HIV infection, free vital gp120 protein may circulate in the blood and the lymph system and bind to the CD4 receptor of uninfected helper T cell, making them susceptible to attack by the immune system. Regardless of how helper T cell are killed by HIV, the decline in number of cells leads to a more general decline in immune functioning leading through the six stages of the disease progression referred to above.

It is believed that colchicine blocks the release of glycoproteins, i.e. gp120, which promote adhesion between the cells as described above. In the development of syncytia, the T4 cells are bound together to create megacells of infected and uninfected leukocytes which cannot carry out their immune function. It is believed that the colchicine dissolves and/or prevents the glycoprotein bond. This action prevents the T4 cells from agglomerating and releases the uninfected leukocytes (T-cells) to be active in an immune response and prevents their death and eventual depletion.

There is also believed to be a synergistic effect in that the liberation of infected T4 cells from the glycoprotein also renders them more available, and hence susceptible, to the microbicidal action of the free radical type components of the electrolyzed saline solution. Moreover, colchicine is a mild immunosuppressant which may slow the replication of the virus lying dormant inside T4 cells. This dormant virus is waiting for an outside infection to stimulate an immune response which will activate viral replication.

The dosage of colchicine may vary between about 1.0 to 3.0 mg. with about 1.5 being considered optimal for adults. It is preferably administered intraveneously just prior to or concurrent with the administration of the electrolyzed saline solution.

To conclude the treatment, about 500 to 1500 mgs, and preferably about 1000 mg. of ascorbic acid, or its sodium salt, is administered about two to twenty minutes after the injection of the electrolyzed saline. This reducing agent neutralizes the remaining unreacted active components of the electrolyzed saline.

The following examples are illustrative of the invention and its use. All electrolyzed saline solutions used were obtained by subjecting about a 0.33% (about one third physiologically normal) saline solution to electrolysis for about 5 to 15 minutes in a Ster-O-Lizer Model 200, manufactured by Ster-O-Lizer Manufacturing Corporation, 2109 West 2300 South in West Valley City, Utah. The voltage between the electrodes was maintained between about 10 and 20 volts at a current of between about 5 and 20 amps. The freshly prepared electrolyzed saline contains about 200 ppm $Cl^-$, along with other electrolysis products selected from the group consisting of ozone, hydroxide, hypochlorite, peroxide, chlorine dioxide and oxygen along with corresponding amounts of molecular hydrogen and sodium and hydrogen ions.

EXAMPLE I

This example records treatment of a patient diagnosed as having cardiomyopathy (viral myocarditis). The patient, a male 40 years of age, was unable to sleep without the aid of an oxygen mask and could only walk a few steps before having to rest. He was sufficiently ill that a heart transplant had been suggested but, due to cost, this procedure was not available. Treatment was begun by an initial intravenous injection of 1.5 mg of colchicine followed by the intravenous injection of 20 cc of a balanced normal saline solution made up by blending 17.5 cc of freshly electrolyzed 0.33% saline with 2.5 cc of 5% hypertonic saline. One hour previous to the injections the patient was given an oral dosage of moderating agents consisting of two tablets, each containing 5000 units of superoxide dismutase, 10,000 units of catalase and 10 mg of L-glutathione. The electrolyzed saline was injected over a two minute period. About five minutes following the injection the patient was given 1000 mg of ascorbic acid intravenously.

Improvement was noticed by the patient almost immediately. He was able to extend his exercises, eventually being able to mow his lawn and return to work. However, improvement is not permanent and the patient requires injections at intervals of about seven to ten days in order to maintain and active life style.

EXAMPLE II

A male, age 36, having been diagnosed three years earlier as having multiple sclerosis was treated with and electrolyzed saline solution. His condition was such that he had not been able to function at his employment and required the assistance of a nurse at home. Prior to treatment he walked wobbling from side to side and could not control his forward progression without taking several backward and side to side steps to maintain his balance. Before being treated he was asked by the physician to demonstrate his incoordination by placing the heel of his left foot on his right knee, then to move his heel from the right knee in a direct line to his right toe. The patient was able, after several tries, to touch the knee with his heel but he was not able to move the heel to the toe in a straight line. With very concerted effort, the foot wavering as much as 10 to 12 inches, he was able to touch his right toe with the left heel.

The patient lay on a treatment table and 1.5 mg of colchicine was first administered followed by the administration 20 cc of electrolyzed saline as in Example I. The same moderating agents as in Example 1 were also administered orally one hour prior to the injection. The entire intravenous injection procedure lasted required about 10 minutes . Again, about five minutes after the last of the electrolyzed saline was administered, the patient was given an intravenous injection of about 1000 mg of ascorbic acid.

There was immediate improvement in muscular control. Following the procedure the patient could readily perform the placement of the left heel on the right knee and move the heel in a direct line from the right knee to the right foot. The patient was able to remove himself from the treatment table and, hesitatingly, take several steps. Over a period of several minutes he was able to walk almost normally.

The treatment is not a cure and the patient requires injections at about one week intervals. Although the results of this treatment are stated in subjective terms, the patient is able to maintain a much more active lifestyle as a result of the electrolyzed saline therapy.

EXAMPLE III

This examples focuses on treatment of an AIDS patient in the last stages of this disease. The patient was a male, age 53, who had tested positive several years earlier as being infected by the HIV virus. He had been hospitalized numerous times and had contracted pneumonia. He was extremely fatigued, had thrush in his mouth along with other usual AIDS related symptoms. This patient, realizing that his death was near, volunteered for treatment with electrolyzed saline.

The patient was injected intravenously, first with 1.5 mg of colchicine followed by 30 cc of the balanced saline [26.25 cc of electrolyzed saline blended with 3.75 cc of 5% hypertonic saline] over a period of approximately 15 minutes followed about five minutes later by intravenous injection of 1000 mg of ascorbic acid. The patient was treated daily for five consecutive days with the same injections. There was no evidence of any abnormal side effects during the treatment period. The patient was monitored with continuous monitoring of a cardiogram. At the beginning of the first injection, the patient demonstrated a very irregular heart rhythm. At the end of the series of injections he showed marked improvement but still had a small amount of irregularity.

Subjectively, the patient stated that he felt better after each injection. His energy level increased daily and he was able to sleep better. The thrush in his mouth was improved. He was able to eat better and the pain associated with his disease was lessened.

Blood tests were conducted each day. There was no decrease in the red blood count and the blood showed no abnormalities or hemolysis. Repeat white blood counts revealed that the patient started with a leukocyte count of about 2000 with 10% lymphocytes. At the end of the fifth day the leukocyte count was 625 with 20% lymphocytes. This means that the patient has a total lymphocyte count of 220 cells/mm$^2$ at first and a total of 525 cells/mm$^2$ at the end of five days.

The above examples show there is evidence that the use of electrolyzed saline in treating the patients in accordance with the invention resulted in marked improvement with no visible toxic side effects.

I claim:

1. A method for the treatment of antigen related infections selected from the group consisting of cardiomyopathy and multiple sclerosis, said method including:
    (a) intravenously injecting an effective amount of colchicine into a human subject followed by,
    (b) intravenously injecting into said subject an effective amount of a isotonic electrolyzed saline solution prepared by subjecting a 0.25 to 0.50% saline solution to electrolysis for a period of time and at sufficient voltage/current to yield an initial electrolyzed solution containing between about 100 to 300 ppm of chloride ions along with other electrolysis products selected from the group consisting of ozone, hydroxide, hypochlorite, peroxide, chlorine dioxide and oxygen along with corresponding amounts of molecular hydrogen and sodium and hydrogen ions followed by balancing said initial electrolyzed solution with sufficient amounts of hypertonic saline to provide said isotonic electrolyzed saline solution; and (c) administering to said subject, in correlation with steps (a) and (b), an effective amount of one or more modulating agents selected from the group consisting of superoxide dismutase, myeloperoxidase, glutathione peroxidase, glutathione, catalase, ascorbic acid and sodium ascorbate.

2. The method according to claim 1 wherein said modulating agent is administered intravenously, parenterally or orally prior to, concurrent with or following step (b).

3. The method according to claim 2 wherein the modulating agent is a member selected from the group consisting of ascorbic acid and sodium ascorbate.

4. The method according to claim 3 wherein said modulating agent is administered intravenously following step (b).

5. The method according to claim 4 wherein the modulating agent is administered in an amount sufficient to reduce or neutralize electrolysis products in said electrolyzed saline solution.

* * * * *